United States Patent [19]

Maurer et al.

[11] Patent Number: 5,405,841
[45] Date of Patent: Apr. 11, 1995

[54] PHOSPHORYLATED AZA COMPOUNDS

[75] Inventors: Fritz Maurer, Ibaraki; Jürgen Hartwig; Christoph Erdelen, both of Leichlingen, all of Germany

[73] Assignee: Bayer Aktiengesellschaft, Leverkusen, Germany

[21] Appl. No.: 150,190

[22] PCT Filed: May 26, 1992

[86] PCT No.: PCT/EP92/01184
§ 371 Date: Nov. 30, 1993
§ 102(e) Date: Nov. 30, 1993

[87] PCT Pub. No.: WO92/21687
PCT Pub. Date: Dec. 10, 1992

[30] Foreign Application Priority Data

Jun. 7, 1991 [DE] Germany .................. 41 18 706.7

[51] Int. Cl.⁶ .................. A61K 31/675; A61K 31/67; A61K 31/665; C07F 9/02
[52] U.S. Cl. ........................ 514/89; 514/85; 514/86; 514/91; 514/92; 514/93; 514/94; 514/95; 514/99; 544/232; 544/243; 544/337; 546/22; 548/111; 548/112; 549/6; 549/218
[58] Field of Search .................. 546/22; 548/111, 112; 514/86, 89, 85, 91–95, 99; 544/232, 243, 337; 549/6, 218

[56] References Cited

U.S. PATENT DOCUMENTS

| 4,154,826 | 5/1979  | Rathgeb ............... 424/211 |
| 4,590,182 | 5/1986  | Haga et al. ............ 514/80 |
| 4,742,060 | 5/1988  | Shiokawa et al. ...... 514/252 |
| 4,880,933 | 11/1989 | Shiokawa et al. ...... 544/332 |

FOREIGN PATENT DOCUMENTS

| 192060  | 8/1986 | European Pat. Off. . |
| 277317  | 8/1988 | European Pat. Off. . |
| 2376155 | 7/1978 | France . |

Primary Examiner—Cecilia Trang
Attorney, Agent, or Firm—Sprung Horn Kramer & Woods

[57] ABSTRACT

The invention relates to new phosphorylated aza compounds, to processes for their preparation and to their use as pesticides, in particular as soil-acting insecticides and nematicide.

The new compounds have the general formula (I)

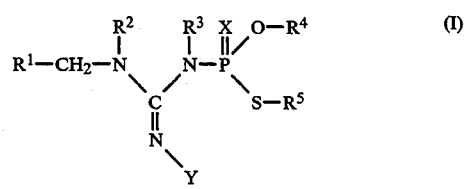

in which $R^1$–$R^5$, X and Y are defined as in the specification, with the exception of compound O-ethyl S-propyl 3-(6-chloro-3-pyridinylmethyl)-2-nitroimino-imidazolidine-1-thiophosphate.

7 Claims, No Drawings

PHOSPHORYLATED AZA COMPOUNDS

This application is the 371 of PCT/EP92/01184, filed May, 26, 1992.

The invention relates to new phosphorylated aza compounds, to processes for their preparation and to their use as pesticides, in particular as soil-acting insecticides and nematicides.

It has been disclosed that certain phosphorylated aza compounds, such as, for example, O-ethyl S-(1-methylpropyl) (2-oxo-3-thiazolidinyl)phosphonothioate/fosthiazate, can be used as insecticides, acaricides and nematicides (cf. U.S. Pat. No. 4,590,182). However, the activity of these known compounds is not entirely satisfactory, in particular at low application rates and concentrations of active compound.

Furthermore, certain optionally phosphorylated aza compounds, such as, for example, N-nitro-1-(6-chloro-3-pyridinyl-methyl)-4,5-dihydro-1H-imidazol-2-amine (imidaclopyrid), diethyl 3-(2-chloro-5-thiazolyl-methyl)-2-nitroimino-imidazolidine-1-phosphonate, dimethyl 3-(6-chloro-3-pyridinyl-methyl)-2-nitroimino-imidazolidine-1-phosphonate, O,O-diethyl 3-(6-chloro-3-pyridinyl-methyl)-2-nitroimino-imidazolidine-1-thiophosphonate, O-ethyl S-propyl 3-(6-chloro-3-pyridinyl-methyl)-2-nitroimino-imidazolidine-1-thiophosphonate and dimethyl 2-nitroimino-3-(3-pyridinyl-methyl)-imidazolidine-1-phosphonate, have been disclosed as potential insecticides (cf. EP-A 192,060 and JP-A 63156786/Chem. Abstracts 110:8210d).

However, nothing has been disclosed about the possibility of also being able to combat at the same time insects and nematodes in the soil, using these compounds.

The present invention relates to the phosphorylated aza compounds of the general formula (I)

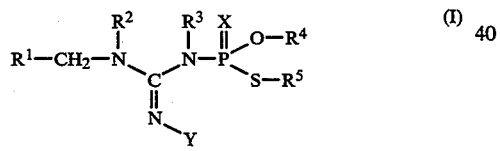

in which
R$^1$ represents a five- or six-membered heterocyclic group which contains 1, 2, 3 or 4 nitrogen atoms and/or one or two oxygen or sulphur atoms as hetero atom ring members, the number of hetero atoms being 1, 2, 3 or 4, and which is optionally substituted by halogen, cyano, nitro, alkyl, halogenoalkyl, alkenyl, halogenoalkenyl, alkinyl, alkoxy, halogenoalkoxy, alkenyloxy, halogenoalkenyloxy, alkinyloxy, alkylthio, halogenoalkylthio, alkenylthio, halogenoalkenylthio, alkinylthio, alkylsulphinyl, halogenoalkylsulphinyl, alkylsulphonyl, halogenoalkylsulphonyl, amino, alkylamino, dialkylamino, aryl, aryloxy, arylthio, arylamino, aralkyl, formylamino, alkylcarbonylamino, formyl, carbamoyl, alkylcarbonyl and/or alkoxycarbonyl, R$^2$ represents hydrogen or alkyl, R$^3$ represents hydrogen or alkyl or together with R$^2$ represents alkanediyl, R$^4$ represents alkyl, R$^5$ represents alkyl, X represents oxygen or sulphur and Y represents nitro or cyano, with the exception of the compound O-ethyl S-propyl 3-(6-chloro-3-pyridinylmethyl)-2-nitroimino-imidazolidine-1-thiophosphonate.

Surprisingly, the compounds of the formula (I) display a considerably more powerful insecticidal activity, in particular against soil-dwelling insects, than the known compound O-ethyl S-(1-methylpropyl) (2-oxo-3-thiazolidnyl)-phosphonothioate and, in contrast to active compounds of the prior art which are related from the point of view of their structure, also have a very powerful activity against soil-dwelling insects and soil-dwelling nematodes.

Formula (I) provides a general definition of the phosphorylated aza compounds according to the invention. In formula (I), R$^1$ preferably represents a five- or six-membered heterocyclic group from the series consisting of furyl, thienyl, pyrrolyl, pyrazolyl, imidazolyl, 1,2,3- or 1,2,4-triazolyl, oxazolyl, isoxazolyl, 1,2,4- or 1,3,4-oxadiazolyl, thiazolyl, isothiazolyl, 1,2,3-, 1,2,4-, 1,2,5- or 1,3,4-thiadiazolyl, pyridyl, pyridazinyl, pyrimidinyl and pyrazinyl, each of which is optionally substituted by fluorine, chlorine, bromine, iodine, cyano, nitro, C$_1$–C$_4$-alkyl (which is optionally substituted by fluorine and/or chlorine), C$_2$–C$_4$-alkenyl (which is optionally substituted by fluorine and/or chlorine), C$_2$–C$_4$-alkinyl, C$_1$–C$_4$-alkoxy (which is optionally substituted by fluorine and/or chlorine), C$_3$–C$_4$-alkenyloxy (which is optionally substituted by fluorine and/or chlorine), C$_3$–C$_4$-alkinyloxy, C$_1$–C$_4$-alkylthio (which is optionally substituted by fluorine and/or chlorine), C$_3$–C$_4$-alkenylthio (which is optionally substituted by fluorine and/or chlorine), C$_3$–C$_4$-alkinylthio, C$_1$–C$_4$-alkylsulphinyl (which is optionally substituted by fluorine and/or chlorine), C$_1$–C$_4$-alkylsulphonyl (which is optionally substituted by fluorine and/or chlorine), amino, C$_1$–C$_4$-alkylamino, di-(C$_1$–C$_4$-alkyl)-amino, phenyl, phenoxy, phenylthio, phenylamino, benzyl, formylamino, C$_1$–C$_4$-alkylcarbonylamino, formyl, carbamoyl, C$_1$–C$_4$-alkylcarbonyl and/or C$_1$–C$_4$-alkoxy-carbonyl, R$^2$ preferably represents hydrogen or C$_1$–C$_3$-alkyl, R$^3$ preferably represents hydrogen or C$_1$–C$_3$-alkyl or together with R$^2$ represents C$_2$–C$_4$-alkanediyl, R$^4$ preferably represents C$_1$–C$_4$-alkyl, R$^5$ preferably represents C$_1$–C$_5$-alkyl, X preferably represents oxygen or sulphur and Y preferably represents nitro or cyano, with the exception of the compound O-ethyl S-propyl 3-(6-chloro-3-pyridinylmethyl)-2-nitroiminoimidazolidine-1-thiophosphonate.

Particularly preferred compounds of the formula (I) are those in which

R$^1$ represents a five- or six-membered heterocyclic group from the series consisting of pyrazolyl, 1,2,4-triazolyl, oxazolyl, isoxazolyl, thiazolyl, isothiazolyl, 1,2,5-thiadiazolyl, pyridyl, pyrazinyl and pyrimidinyl, each of which is optionally substituted by fluorine, chlorine, bromine, cyano, nitro, C$_1$–C$_2$-alkyl (which is optionally substituted by fluorine and/or chlorine), C$_1$–C$_2$-alkoxy (which is optionally substituted by fluorine and/or chlorine), C$_1$–C$_2$-alkylthio (which is optionally substituted by fluorine and/or chlorine) or C$_1$–C$_2$-alkylsulphonyl (which is optionally substituted by fluorine and/or chlorine), R$^2$ represents hydrogen or methyl, $R^3$ represents hydrogen or methyl or together with $R^2$ represents dimethylene or trimethylene, $R^4$ represents ethyl, propyl or isopropyl, $R^5$ represents ethyl, propyl, isopropyl, butyl, isobutyl or sec-butyl, X represents oxygen or sulphur and Y represents nitro or cyano, with the exception of the compound O-ethyl S-propyl 3-(6-chloro-3-pyridinylmethyl)-2-nitroimino-imidazolidine-1-thiophosphonate.

Very particularly preferred new compounds of the formula (I) are those in which $R^1$ represents 6-chloro-3-pyridinyl or 2-chloro-5-thiazolyl, $R^2$ and $R^3$ together represent dimethylene (—CH$_2$CH$_2$—) or trimethylene (—CH$_2$CH$_2$CH$_2$—)

$R^4$ represents ethyl, $R^5$ represents sec-butyl,

X represents oxygen or sulphur and

Y represents nitro.

The compounds of the formula (I) are obtained when (a) aza compounds of the general formula (II)

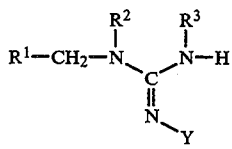

in which $R^1$, $R^2$, $R^3$ and Y have the abovementioned meaning, are reacted with-chloro(di)thiophosphoric acid O,S-diesters of the general formula (III)

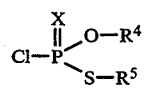

in which $R^4$, $R^5$ and X have the abovementioned meaning, if appropriate in the presence of an acid acceptor and, if appropriate, in the presence of a diluent, or when (b) heterocyclylmethyl chlorides of the general formula (IV)

$$R^1\text{—CH}_2\text{—Cl} \quad \text{(IV)}$$

in which $R^1$ has the abovementioned meaning, are reacted with phosphorylated aza compounds of the general formula (V)

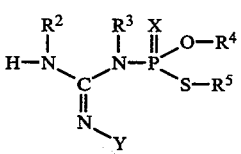

in which $R^2$, $R^3$, $R^4$, $R^5$, X and Y have the abovementioned meaning, if appropriate in the presence of an acid acceptor and, if appropriate, in the presence of a diluent.

If, for example, 1-(2-chloro-5-thiazolyl-methyl)-2-nitro-imino-imidazolidine and O-ethyl S-sec-butyl chlorodithiophosphate are used as starting substances, the sequence of the reaction in process (a) according to the invention can be outlined by the following equation:

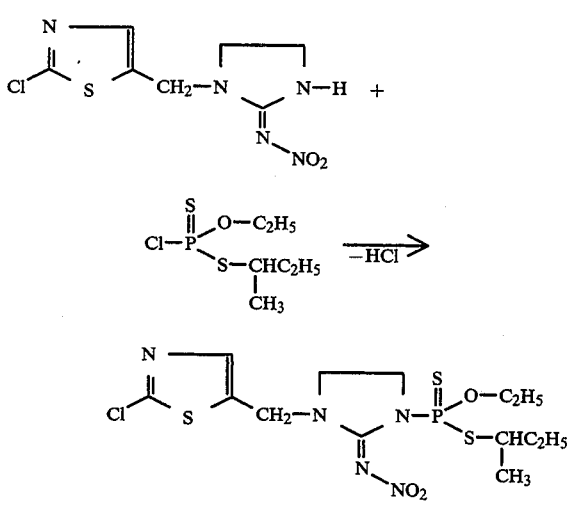

If, for example, 6-chloro-3-chloromethyl-pyridine and O-ethyl S-isopropyl 2-cyanoimino-imidazolidine-1-thiophosphonate are used as starting substances, the sequence of the reaction in process (b) according to the invention can be outlined by the following equation:

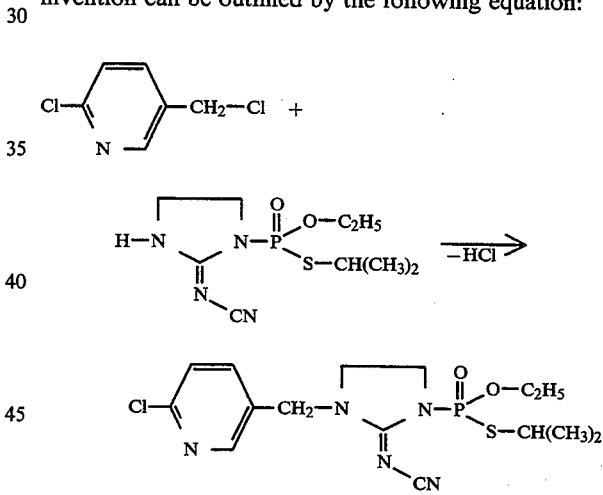

Formula (II) provides a general definition of the aza compounds to be used as starting substances in process (a) according to the invention for the preparation of compounds of the formula (I).

In formula (II), $R^1$, $R^2$, $R^3$ and Y preferably, or in particular, have those meanings which have already been mentioned in connection with the description of the compounds of the formula (I) according to the invention as being preferred, or particularly preferred, for $R^1$, $R^2$, $R^3$ and Y.

The starting substances of the formula (II) are known and/or can be prepared by processes known per se (cf. EP-A 192,060).

Formula (III) provides a general definition of the chloro-(di) thiophosphoric acid O,S-diesters furthermore to be used as starting substances in process (a) according to the invention.

In formula (III), $R^4$, $R^5$ and X preferably, or in particular, have those meanings which have already been mentioned above in connection with the description of the compounds of the formula (I) according to the invention as being preferred, or particularly preferred, for $R^4$, $R^5$ and X.

The starting substances of the formula (III) are known and/or can be prepared by processes known per se (cf. DE-A 2,527,308; DE-A 2,615,342; DE-A 2,642,982; DE-A 2,804,796).

Formula (IV) provides a general definition of the heterocyclylmethyl chlorides to be used as starting substances in process (b) according to the invention for the preparation of compounds of the formula (I).

In formula (IV), $R^1$ preferably, or in particular, has the meaning which has already been mentioned above in connection with the description of the compounds of the formula (I) according to the invention as being preferred, or particularly preferred, for $R^1$.

The starting substances of the formula (IV) are known and/or can be prepared by processes known per se (cf. J. Heterocycl. Chem. 16 (1979), 333–337).

Formula (V) provides a general definition of the phosphorylated aza compounds furthermore to be used as starting substances in process ( b ) according to the invention.

In formula (V), $R^2$, $R^3$, $R^4$, $R^5$, X and Y preferably, or in particular, have the meanings which have already been mentioned above in connection with the description of the compounds of the formula (I) according to the invention as being preferred, or particularly preferred, for $R^2$, $R^3$, $R^4$, $R^5$, X and Y.

The starting substances of the formula (V) are known and/or can be prepared by processes known per se (cf. EP-A 277,317).

Processes (a) and (b) according to the invention for the preparation of the compounds of the formula (I) are preferably carried out using diluents. Diluents which are suitable are virtually all inert organic solvents. These preferably include aliphatic and aromatic, optionally halogenated hydrocarbons, such as pentane, hexane, heptane, cyclohexane,-petroleum ether, benzine, ligroin, benzene, toluene, xylene, methylene chloride, ethylene chloride, chloroform, carbon tetrachloride, chlorobenzene and o-dichlorobenzene, ethers, such as diethyl ether and dibutyl ether, glycol dimethyl ether and diglycol dimethyl ether, tetrahydrofuran and dioxane, ketones, such as acetone, methyl ethyl ketone, methyl isopropyl ketone and methyl isobutyl ketone, esters, such as methyl acetate and ethyl acetate, nitriles, such as, for example, acetonitrile and propionitrile, amides, such as, for example, dimethylformamide, dimethylacetamide and N-methyl-pyrrolidone, and also dimethyl sulphoxide, tetramethylene sulphone and hexamethylphosphoric triamide.

Acid acceptors which can be employed in processes (a) and (b) according to the invention are all acid-binding agents which can customarily be used for reactions of this type. The following are preferably suitable: alkali metal hydrides and alkaline earth metal hydrides, such as lithium hydride, sodium hydride, potassium hydride and calcium hydride, alkali metal carbonates, alkali metal hydrogen carbonates, alkaline earth metal carbonates and alkaline earth metal hydrogen carbonates, such as sodium carbonate, potassium carbonate, sodium hydrogen carbonate and potassium hydrogen carbonate and also calcium carbonate, alkali metal acetates, such as sodium acetate and potassium acetate, alkali metal alcoholates, such as sodium tert-butylate and potassium tert-butylate, furthermore basic nitrogen compounds, such as trimethylamine, triethylamine, tripropylamine, tributylamine, diisobutylamine, dicyclohexylamine, ethyldiisopropylamine, ethyldicyclohexylamine, N,N-dimethylbenzylamine, N,N-dimethyl-aniline, pyridine, 2-methyl-, 3-methyl-, 4-methyl-, 2,4-dimethyl-, 2,6-dimethyl-, 2-ethyl-, 4-ethyl- and 5-ethyl-2-methyl-pyridine, 1,5-diazabicyclo-[4,3,0]-non-5-ene (DBN), 1,8-diazabicyclo[5,4,0]-undec-7-ene (DBU) and 1,4-diazabicyclo-[2,2,2]-octane (DABCO).

When carrying out process (a) according to the invention, the reaction temperatures can be varied within a substantial range. In general, the process is carried out at temperatures between $-20°$ C. and $+80°$ C. preferably at temperatures between $0°$ C. and $50°$ C.

When carrying out process (b) according to the invention, the reaction temperatures can be varied within a substantial range. In general, the process is carried out at temperatures between $0°$ C. and $120°$ C. preferably at temperatures between $20°$ C. and $80°$ C.

Processes (a) and (b) according to the invention are generally carried out under atmospheric pressure. However, they can also be carried out under elevated or reduced pressure.

To carry out processes (a) and (b) according to the invention, the starting substances required in each case are generally employed in approximately equimolar amounts. However, it is also possible to use a larger excess of one of the two components employed in each case. In general, the reactions are carried out in a suitable diluent in the presence of an acid acceptor, and the reaction mixture is stirred for several hours at the temperature required in each case. Working-up is carried out in each case by customary methods (cf. the Preparation Examples).

The compounds of the general formula (I) are suitable for combating animal pests, preferably arthropods and nematodes, in particular insects, and nematodes in the soil, encountered in agriculture, in forestry, in the protection of stored products and of materials, and in the hygiene field. They are active against normally sensitive and resistant species and against all or some stages of development. The abovementioned pests include:

From the order of the Isopoda, for example, *Oniscus asellus, Armadillidium vulgare* and *Porcellio scaber.* From the order of the Diplopoda, for example, *Blaniulus guttulatus*. From the order of the Chilopoda, for example, *Geophilus carpophagus* and Scutigera spec. From the order of the Symphyla, for example, *Scutigerella immaculata*. From the order of the Thysanura, for example, *Lepisma saccharina*. From the order of the Collembola, for example, *Onychiurus armatus*. From the order of the Orthoptera, for example, *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria*. From the order of the Dermaptera, for example, *Forficula auricularia*. From the order of the Isoptera, for example, Reticulitermes spp. From the order of the Anoplura, for example, *Phylloxera vastatrix,* Pemphigus spp., *Pediculus humanus corporis,* Haematopinus spp. and Linognathus spp. From the order of the Mallophaga, for example, Trichodectes spp. and Damalinea spp. From the order of the Thysanoptera, for example, *Hercinothrips femoralis* and *Thrips tabaci*. From the order of the Heteroptera, for example, Eurygaster spp., *Dysdercus intermedius, Piesma quadrata, Cimex lectularius, Rhodnius prolixus* and Triatoma spp. From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. Psylla spp. From the order of the Lepidoptera, for example, *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Hellothis spp., *Spodoptera exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima* and *Tortrix viridana.*

From the order of the Coleoptera, for example, *Anobium punctatum, Rhizopertha dominica, Acanthoscelides obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varive stis,* Atomaria spp., *Oryzaephilus surinamensis,* Antho nomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Cono derus spp., *Melolontha melolontha, Amphimallon solsti tialis* and *Costelytra zealandica.* From the order of the Hymenoptera, for example, Diprion spp., Hoplocampa spp., Lasius spp., *Monomorium pharaonis* and Vespa spp. From the order of the Diptera, for example, Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa.*

From the order of the Siphonaptera, for example, *Xenopsylla cheopis* and Ceratophyllus spp. From the order of the Arachnida, for example, *Scorpio maurus* and *Latrodectus mactans.*

From the order of the Acarina, for example, *Acarus siro,* Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The phytoparasitic nematodes include *Pratylenchus spp., Radopholus similis, Ditylenchus dipsaci, Tylenchulus semipenetrans, Heterodera spp., Meloidogyne spp., Aphelenchoides spp., Longidorus spp., Xiphinema spp.* and *Trichodorus spp.*

The compounds of the formula (I) according to the invention are distinguished by an outstanding insecticidal and nematicidal activity. In particular when used against leaf- and soil-dwelling insects which are harmful to plants, they display a very powerful activity, and also against nematodes. The excellent (root-systemic) activity against soil-dwelling insects and nematodes must be particularly emphasised.

Depending on their particular physical and/or chemical properties, the active compounds can be converted to the customary formulations, such as solutions, emulsions, suspensions, powders, foams, pastes, granules, aerosols, natural and synthetic materials impregnated with active compound, very fine capsules in polymeric substances and in coating compositions for seed, furthermore formulations used with burning equipment, such as fumigating cartridges, fumigating cans, fumigating coils and the like, as well as ULV cold mist and warm mist formulations.

These formulations are produced in a known manner, for example by mixing the active compounds with extenders, that is liquid solvents, liquefied gases under pressure, and/or solid carriers, optionally with the use of surface-active agents, that is emulsifying agents and-/or dispersing agents, and/or foam-forming agents. In the case of the use of water as an extender, organic solvents can, for example, also be used as auxiliary solvents. As liquid solvents, there are suitable in the main: aromatics, such as xylene, toluene or alkylnaphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethyl sulphoxide, as well as water; by liquefied gaseous extenders or carriers are meant liquids which are gaseous at ambient temperature and under atmospheric pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, as well as synthetic granules of inorganic and organic meals, and granules of organic material such as sawdust, coconut shells, maize cobs and tobacco stalks; as emulsifying and/or foam-forming agents there are suitable: for example non-ionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates as well as albumen hydrolysis products; as dispersing agents there are suitable: for example lignin-sulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as natural phospholipids, such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations in general contain between 0.1 and 95 per cent by weight of active compound, preferably between 0.5 and 90%.

The active compounds can be present in their commercially available formulations and in the use forms, prepared from these formulations, as a mixture with other active compounds, such as insecticides, attractants, sterilising agents, acaricides, nematicides, fungicides, growth-regulating substances or herbicides. The insecticides include, for example, phosphates, carbamates, carboxylates, chlorinated hydrocarbons, phenylureas and substances produced by microorganisms, inter alia.

The active compounds can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

USE EXAMPLES

In the use examples, the compounds (A) and (B) listed below are used as comparison compounds:

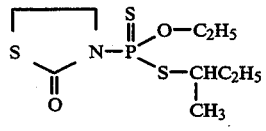
(A)

O-Ethyl S-(1-methylpropyl) (2-oxo-3-thiazolidinyl)-phosphonothioate/fosthiazate (disclosed in U.S. Pat. Specification No. 4,509,182).

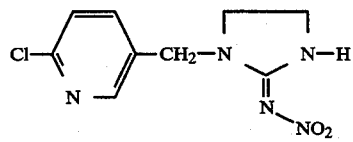
(B)

N-Nitro-1-(6-chloro-3-pyridinyl-methyl)-4,5-dihydro-1H-imidazole-2-amine/imidacloprid (disclosed in EP-A 192,060).

Example A

Critical concentration test/soil insects
Test insect: Diabrotica balteata larvae in the soil
Solvent: 4 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration. The concentration of the active compound in the preparation is of practically no importance here, only the amount by weight of active compound per unit volume of soil, which is given in ppm (mg/l), being decisive. The soil is transferred into 0.5 l pots and the pots are left to stand at 20° C.

Immediately after setting up the experiment, 5 pregerminated maize kernels are placed into each pot. After 1 day, the test insects in question are introduced into the treated soil. After a further 7 days the degree of effectiveness of the active compound is determined in % by counting the dead and live test insects. The degree of effectiveness is 100% if all the test insects have been killed and is 0% if just as many test insects are still alive as in the case of the untreated control.

In this test, the compound of Preparation Example 1 showed a degree of destruction of 95% at an active compound concentration of 10 ppm, while the known active compound (A) showed no effect at the same concentration.

Example B

Critical concentration test/root-systemic action
Test insect: Myzus persicae
Solvent: 4 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil. The concentration of the active compound in the preparation is of practically no importance, only the amount by weight of active compound per unit volume of soil, which is given in ppm (=mg/l), being decisive. The treated soil is transferred into pots and these are planted with cabbage (Brassica oleracea). The active compound can in this way be taken up from the soil by the roots of the plants and be transported into the leaves.

To demonstrate the root-systemic effect, the leaves are infested with the abovementioned test animals after 7 days. After a further 2 days, the evaluation is made by counting or estimating the dead animals. The root-systemic action of the active compound is deduced from the destruction figures. It is 100% if all test animals have been killed and 0% if just as many test insects are still alive as in the case of the untreated control.

In this test, the compounds of Preparation Examples 1 and 2 were fully active at an active compound concentration of 2.5 ppm (degree of destruction 100%), while the comparison compound (A) showed no effect under the same conditions.

Example C

Critical concentration test/nematodes
Test nematode: Meloidogyne incognita
Solvent: 4 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil which is severely infested with the test nematode. The concentration of the active compound in the preparation is of practically no importance, only the amount of active compound per unit volume of soil, which is given in ppm (=mg/l), being decisive. The treated soil is transferred into pots, lettuce is sown, and the pots are kept at a greenhouse temperature of 25° C.

After four weeks, the lettuce roots are examined for nematode infestation (root galls), and the degree of effectiveness is 100% if infestation is avoided completely and 0% if the level of infestation is just as high as in the control plants in untreated, but equally infested, soil.

In this test, the compound of Preparation Example 1 showed a degree of destruction of 100% at an active compound concentration of 20 ppm.

Under these conditions, comparison compound (B) exhibited no activity against the test nematode *Meloidogyne incognita*.

Example D

Critical concentration test/nematodes
Test nematode: Globodera rostochiensis
Solvent: 4 parts by weight of acetone
Emulsifier: 1 part by weight of alkylaryl polyglycol ether To produce a suitable preparation of active compound, 1 part by weight of active compound is mixed with the stated amount of solvent, the stated amount of emulsifier is added and the concentrate is diluted with water to the desired concentration.

The preparation of active compound is intimately mixed with soil which is severely infested with the test nematode. The concentration of the active compound in the preparation is of practically no importance, only the amount of active compound per unit volume of soil, which is given in ppm (=mg/l), being decisive. The treated soil is transferred into pots, potatoes are planted, and the pots are kept at a greenhouse temperature of 20° C.

After 6 weeks, the potato roots are examined for cysts, and the degree of effectiveness of the active compound is determined in %. The degree of effectiveness is 100% if infestation is avoided completely and 0% if the level of infestation is just as high as in the control plants in untreated, but equally infested, soil.

In this test, the compound of Preparation Example 1 showed a degree of destruction of 100% at an active compound concentration of 20 ppm.

Under these conditions, comparison compound (B) exhibited no activity against the test nematode *Globodera rostochiensis*.

Example E

Seed treatment test/soil insects
Test insect: *Diabrotica balteata* larvae in the soil
Test plant: *Zea mays*
Solvent: 1 part by weight of acetone
Excipient: kaolin To produce a suitable preparation of active compound, the active compound is dissolved in acetone and 1 part by weight of active compound/acetone is mixed with 5 parts by weight of kaolin. The maize seed is treated with this active compound preparation at the application rates required. It is sown in 0.5 l pots containing standardised soils at a greenhouse temperature of 20° C.

After 1 day, approx. 30 *Diabrotica larvae* are placed into each pot. After a further 7 days, the degree of action is determined in % by counting the dead and live test insects. The degree of action of 100% when all test insects have been destroyed, it is 0% when just as many test insects are alive as in the untreated control.

In this test, the compound of Preparation Example 1 caused a degree of destruction of 100% at an active compound concentration of 0.5 g/kg of seed, while compound (A) showed no effect under the same conditions.

Example F

Seed treatment test/root-systemic action
Test insect: *Aphis fabae*
Test plant: *Vicia faba*
Solvent: 1 part by weight of acetone
Excipient: kaolin To produce a suitable preparation of active compound, the active compound is dissolved in acetone and 1 part by weight of active compound/acetone is mixed with 5 parts by weight of kaolin. The bean seed is treated with this preparation of active compound at the application rates required. The field beans are sown in 0.5 l pots containing standardised soils at room temperatures of 20° C.

The active compound can thus be taken up from the soil by the plant roots and transported into the leaves.

For detection of the root-systemic effect, the leaves only are infested with the abovementioned test animals after 14 days. After a further 3 days, the evaluation is carried out by counting or estimating the dead animals. The root-systemic action of the active compound is derived from the destruction figures. It is 100% if all the test animals have been killed and 0% if just as many test insects are still alive as in the untreated control.

In this test, the compound of Preparation Example 1 caused a degree of destruction of 100% at an active compound concentration of 0.25 g/kg of seed, while compound (A) showed no effect under the same conditions.

Example G

Phaedon larvae test
Solvent: 7 parts by weight of dimethyl formamide
Emulsifier: 1 part by weight of alkylaryl polyglycol ether To produce a suitable preparation of active compound, 1 part by weight of active compound is mixed with the stated amount of solvent and the stated amount of emulsifier, and the concentrate is diluted with water to the desired concentration.

Cabbage leaves (*Brassica oleracea*) are treated by being dipped into the preparation of the active compound of the desired concentration and are infested with mustard beetle larvae (*Phaedon cochleariae*) while the leaves are still moist.

After the specified periods of time, the destruction in % is determined. 100% means that all the beetle larvae have been killed; 0% means that none of the beetle larvae have been killed.

In this test, a superior activity compared with the comparison compound (A) is shown, for example, by the following compounds of the preparation examples: 1 and 2.

PREPARATION EXAMPLES

Example 1

(Process (a))

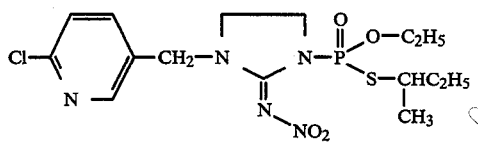

6.7 g (0.06 mol) of potassium tert-butanolate are added at 25°–30° C. to a mixture of 12.7 g (0.05 mol) of 1-(6-chloro-3-pyridinylmethyl)-2-nitroimino-imidazolidine and 80 ml of tetrahydrofuran. This solution is treated, at 5° C., with 10.9 g (0.05 mol) of S-sec-butyl O-ethyl chlorothiophosphate, and stirring is continued overnight at room temperature. The solvent is then removed by distillation in vacuo, and 100 ml of ethyl acetate and 100 ml of water are added. The mixture is shaken; the organic phase is then separated off. It is dried over sodium sulphate and evaporated in vacuo. Remaining volatile components are stripped from the residue at 60° C. under an oil-pump vacuum.

16.7 g (77% of theory) of O-ethyl S-sec-butyl 3-(6-chloro-3-pyridinyl methyl)-2-nitroimino-imidazolidine-1-thiophosphonate are obtained as a yellow oil of refractive index $[\alpha]_D^{23}=1.5655$.

Example 2

O-Ethyl S-sec-butyl 3-(6-chloro-3-pyridinyl-methyl)-2-nitroimino-imidazolidine-1-dithiophosphonate of refractive index $[\alpha]_D^{23}=1.5960$

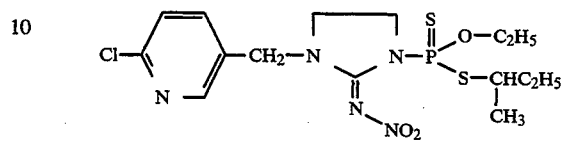

is also obtained analogously to Example 1.

Other compounds of the formula (I)

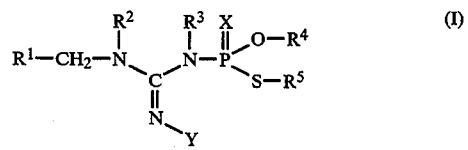

(I)

which can be prepared analogously to Examples 1 and 2 are the following:

TABLE

| Ex. No. | R¹ | R² | R³ | R⁴ | R⁵ | X | Y | Physical constants |
|---|---|---|---|---|---|---|---|---|
| 3 | F-pyridinyl | —CH₂—CH₂— | | C₂H₅ | —CHC₂H₅ / CH₃ | O | NO₂ | |
| 4 | F-pyridinyl | —CH₂—CH₂— | | C₂H₅ | —CHC₂H₅ / CH₃ | S | NO₂ | |
| 5 | Cl-pyridinyl | —(CH₂)₃— | | C₂H₅ | —CHC₂H₅ / CH₃ | O | NO₂ | |
| 6 | Cl-pyridinyl | —(CH₂)₃— | | C₂H₅ | —CHC₂H₅ / CH₃ | S | NO₂ | |
| 7 | Cl-pyridinyl | H | CH₃ | C₂H₅ | —CHC₂H₅ / CH₃ | O | NO₂ | |
| 8 | Cl-pyridinyl | CH₃ | H | C₂H₅ | —CHC₂H₅ / CH₃ | O | NO₂ | |
| 9 | Cl-pyridinyl | CH₃ | CH₃ | C₂H₅ | —CHC₂H₅ / CH₃ | O | NO₂ | |

TABLE-continued

| Ex. No. | R¹ | R² | R³ | R⁴ | R⁵ | X | Y | Physical constants |
|---|---|---|---|---|---|---|---|---|
| 10 | 2-chloro-pyridin-5-yl | $CH_3$ | $CH_3$ | $C_2H_5$ | $-CHC_2H_5$ / $CH_3$ | S | $NO_2$ | |
| 11 | 2-chloro-thiazol-5-yl | | $-CH_2-CH_2-$ | $C_2H_5$ | $-CHC_2H_5$ / $CH_3$ | O | $NO_2$ | |
| 12 | 2-chloro-thiazol-5-yl | | $-CH_2-CH_2-$ | $C_2H_5$ | $-CHC_2H_5$ / $CH_3$ | S | $NO_2$ | |
| 13 | 2-chloro-thiazol-5-yl | | $-(CH_2)_3-$ | $C_2H_5$ | $-CHC_2H_5$ / $CH_3$ | O | $NO_2$ | |
| 14 | 2-chloro-thiazol-5-yl | | $-(CH_2)_3-$ | $C_2H_5$ | $-CHC_2H_5$ / $CH_3$ | S | $NO_2$ | |
| 15 | 2-chloro-pyridin-5-yl | | $-CH_2-CH_2-$ | $C_3H_7$ | $-CHC_2H_5$ / $CH_3$ | O | $NO_2$ | |
| 16 | 2-chloro-pyridin-5-yl | | $-CH_2-CH_2-$ | $C_2H_5$ | $-CH(CH_3)_2$ | O | $NO_2$ | |

We claim:

1. Phosphorylated aza compounds of the formula (I)

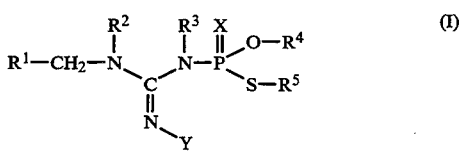

in which

R¹ represents a five- or six-membered heterocyclic group selected from the group consisting of furyl, thienyl, pyrrolyl, pyrazolyl, imidazolyl, 1,2,3- or 1,2,4-triazolyl, oxazolyl, isoxazolyl, 1,2,4- or 1,3,4-oxadiazolyl, thiazolyl, isothiazolyl, 1,2,3-, 1,2,4-, 1,2,5- or 1,3,4-thiadiazolyl, pyridyl, pyridazinyl, pyrimidinyl and pyrazinyl, each of which is optionally substituted by fluorine, chlorine, bromine, iodine, cyano, nitro, $C_1$–$C_4$-alkyl (which is optionally substituted by fluorine and/or chlorine), $C_2$–$C_4$-alkenyl (which is optionally substituted by fluorine and/or chlorine), $C_2$–$C_4$-alkinyl, $C_1$–$C_4$-alkoxy (which is optionally substituted by fluorine and/or chlorine), $C_3$–$C_4$-alkenyloxy (which is optionally substituted by fluorine and/or chlorine), $C_3$–$C_4$-alkinyloxy, $C_1$–$C_4$-alkylthio (which is optionally substituted by fluorine and/or chlorine), $C_3$–$C_4$-alkenylthio (which is optionally substituted by fluorine and/or chlorine), $C_3$–$C_4$-alkinylthio, $C_1$–$C_4$-alkylsulphinyl (which is optionally substituted by fluorine and/or chlorine), $C_1$–$C_4$-alkylsulphonyl (which is optionally substituted by fluorine and/or chlorine), amino, $C_1$–$C_4$-alkylamino, di-($C_1$–$C_4$-alkyl)-amino, phenyl, phenoxy, phenylthio, phenylamino, benzyl, formylamino, $C_1$–$C_4$-alkylcarbonylamino, formyl, carbamoyl, $C_1$–$C_4$-alkylcarbonyl and/or $C_1$–$C_4$-alkoxy-carbonyl, R² represents hydrogen or $C_1$–$C_3$-alkyl, R³ represents hydrogen or $C_1$–$C_3$-alkyl or together with R² represents $C_2$–$C_4$-alkanediyl, R⁴ represents $C_1$–$C_4$-alkyl, R⁵ represents $C_1$–$C_5$-alkyl, X represents oxygen or sulphur and Y represents nitro or cyano, with the exception of the compound O-ethyl S-propyl 3-(6-chloro-3-pyridinylmethyl)-2-nitroimino-imidazolidine-1-thiophosphonate.

2. Compounds of the formula (I) according to claim 1 wherein in that

R¹ represents a five- or six-membered heterocyclic group selected from the group consisting of pyrazolyl, 1,2,4-triazolyl, oxazolyl, isoxazolyl, thiazolyl, isothiazolyl, 1,2,5-thiadiazolyl, pyridyl, pyrazinyl and pyrimidinyl, each of which is optionally substituted by fluorine, chlorine, bromine, cyano, nitro, $C_1$–$C_2$-alkyl (which is optionally substituted by fluorine and/or chlorine), $C_1$–$C_2$-alkoxy (which is optionally substituted by fluorine and/or chlorine), $C_1$-$C_2$-alkylthio (which is optionally substituted by fluorine and/or chlorine) or $C_1$-$C_2$-alkyl sulphonyl (which is optionally substituted by fluorine and/or chlorine), $R^2$ represents hydrogen or methyl, $R^3$ represents hydrogen or methyl or together with $R^2$ represents dimethylene or trimethylene, $R^4$ represents ethyl, propyl or isopropyl, $R^5$ represents ethyl, propyl, isopropyl, butyl, isobutyl or sec-butyl, X represents oxygen or sulphur and Y represents nitro or cyano, with the exception of the compound O-ethyl S-propyl 3-(6-chloro-3-pyridinylmethyl)-2-nitroimino-imidazolidine-1-thiophosphonate.

3. Compounds of the formula (I) according to claim 1 wherein in that $R^1$ represents 6-chloro-3-pyridinyl or 2-chloro-5-thiazolyl, $R^2$ and $R^3$ together represent dimethylene (—CH$_2$CH$_2$—) or trimethylene (—CH$_2$CH$_2$CH$_2$—)

$R^4$ represents ethyl, $R^5$ represents sec-butyl,

X represents oxygen or sulphur and

Y represents nitro.

4. A pesticidal composition comprising a pesticidally effective amount of at least one phosphorylated aza compound of the formula (I) according to claim 1 and an extender.

5. A method of combating animal pests comprising applying to said animal pests or their habitat a pesticidally effective amount of at least one phosphorylated aza compound of the formula (I) according to claim 1.

6. The method according to claim 5, wherein said animal pests are soil-dwelling nematodes.

7. The method according to claim 5, wherein said animal pests are soil-dwelling insects.

* * * * *